United States Patent
Vanden Hoek et al.

(10) Patent No.: US 7,297,104 B2
(45) Date of Patent: Nov. 20, 2007

(54) SEAM CLOSURE DEVICE AND METHODS

(76) Inventors: John Vanden Hoek, 11473 199th Ave., Elk River, MN (US) 55330; Kurt Krueger, 29042 Hillcrest Dr., Stacy, MN (US) 55079; Jeremy Wardour, 12426 Quinn St., NW., Coon Rapids, MN (US) 55448; Jody Rivers, 12890 Omo Pkwy., Elk River, MN (US) 55330

( * ) Notice: Subject to any disclaimer, the term of this patent is extended or adjusted under 35 U.S.C. 154(b) by 749 days.

(21) Appl. No.: 10/790,938

(22) Filed: Mar. 1, 2004

(65) Prior Publication Data

US 2005/0192474 A1 Sep. 1, 2005

(51) Int. Cl.
*A61F 2/00* (2006.01)
*A61B 19/00* (2006.01)

(52) U.S. Cl. ......................................... 600/37; 128/898

(58) Field of Classification Search ................ 128/897, 128/898; 600/16–18, 37; 606/139, 144, 606/148
See application file for complete search history.

(56) References Cited

U.S. PATENT DOCUMENTS

| | | | |
|---|---|---|---|
| 1,982,207 A * | 11/1934 | Furniss | ....................... 606/148 |
| 5,702,343 A | 12/1997 | Alferness | |
| 6,085,754 A | 7/2000 | Alferness et al. | |
| 6,123,662 A | 9/2000 | Alferness et al. | |
| 6,155,972 A | 12/2000 | Nauertz et al. | |
| 6,169,922 B1 | 1/2001 | Alferness et al. | |
| 6,193,648 B1 | 2/2001 | Krueger | |
| 6,230,714 B1 | 5/2001 | Alferness et al. | |
| 6,241,654 B1 | 6/2001 | Alferness | |
| 6,293,906 B1 | 9/2001 | Vanden Hoek et al. | |
| 6,416,459 B1 | 7/2002 | Haindl | |
| 6,425,856 B1 * | 7/2002 | Shapland et al. | ............. 600/37 |
| 6,482,146 B1 | 11/2002 | Alferness et al. | |
| 6,564,094 B2 | 5/2003 | Alferness et al. | |
| 6,572,533 B1 | 6/2003 | Shapland et al. | |
| 2004/0059181 A1 * | 3/2004 | Alferness | ...................... 600/16 |

FOREIGN PATENT DOCUMENTS

JP 2271829 11/1990

\* cited by examiner

*Primary Examiner*—Samuel G. Gilbert
(74) *Attorney, Agent, or Firm*—Faegre & Benson LLP (57) ABSTRACT

A method for tightening a cardiac support device includes forming offsets in excess material in the cardiac support device and inserting a fastener through the offsets. A device for tightening a cardiac support device includes first and second clamp members moveable into and out of mateable engagement. Each of the first and second clamp members includes offset-forming structure.

16 Claims, 9 Drawing Sheets

FIG. 10

SEAM CLOSURE DEVICE AND METHODS

TECHNICAL FIELD

This disclosure relates to apparatus and methods for treating heart disease, particularly congestive heart disease and related heart disfunctions. More particularly, this disclosure relates to apparatus and methods for securing a cardiac support device to a heart.

BACKGROUND

Congestive heart disease is a progressive and debilitating illness. The disease is characterized by a progressive enlargement of heart. As the heart enlarges, the heart is performing an increasing amount of work in order to pump blood for each heart beat. In time, the heart becomes so enlarged that the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

The assignee of this disclosure has developed a device that can be placed on an enlarged heart and fit snugly. One implementation of the assignee's device is characterized as a knit jacket device that is fit around a heart and then secured thereto through a variety of means. The jacket helps to constrain cardiac expansion beyond a predetermined limit. Examples of useable jackets are described in U.S. Pat. Nos. 5,702,343; 6,123,662; 6,241,654; 6,085,754; 6,230,714; 6,169,922; 6,155,972; 6,193,648; 6,293,906; 6,482,146; 6,425,856; 6,572,533; 6,564,094; and 6,416,459. Each of the foregoing patents is incorporated herein by reference.

Improvements in securing cardiac support devices to hearts are desirable.

SUMMARY

In accordance with principles of this disclosure, a method is provided for operably securing a cardiac support device to a mammalian heart. In general, the method includes gathering excess material in a cardiac support device that is loosely positioned around the heart. The cardiac support device includes a jacket having flexible material. The method includes gathering excess material to form an aligned region; simultaneously forming a plurality of offsets in the aligned region; and inserting a fastener through the offsets.

In accordance with principles of this disclosure, a device is provided for closing a slot in a cardiac support device operably positioned around a heart. The device includes a jaw arrangement with cooperating pleat forming members. The pleat forming members are sized to form pleats in excess jacket material.

DETAILED DESCRIPTION

One embodiment of a cardiac support device useable with techniques described herein is shown generally in FIGS. 1-5 at 20. The cardiac support device 20, when operably secure onto the heart of a mammal, will limit the outward expansion of the heart wall during diastolic chamber filling beyond a predetermined size. By "operably secured", it is meant that the device 20 is oriented to enclose portions of the heart and is tightened so there is no excess material or loose slack in the device 20. By "tightened", it is meant that the device 20 will not be worked loose from the heart under normal conditions. The expansion constraint applied to the heart by the cardiac support device 20 is determined by the physician based upon, for example, cardiac output performance or cardiac volume. The cardiac support device 20 provides cardiac reinforcement during diastole.

Figure 1:
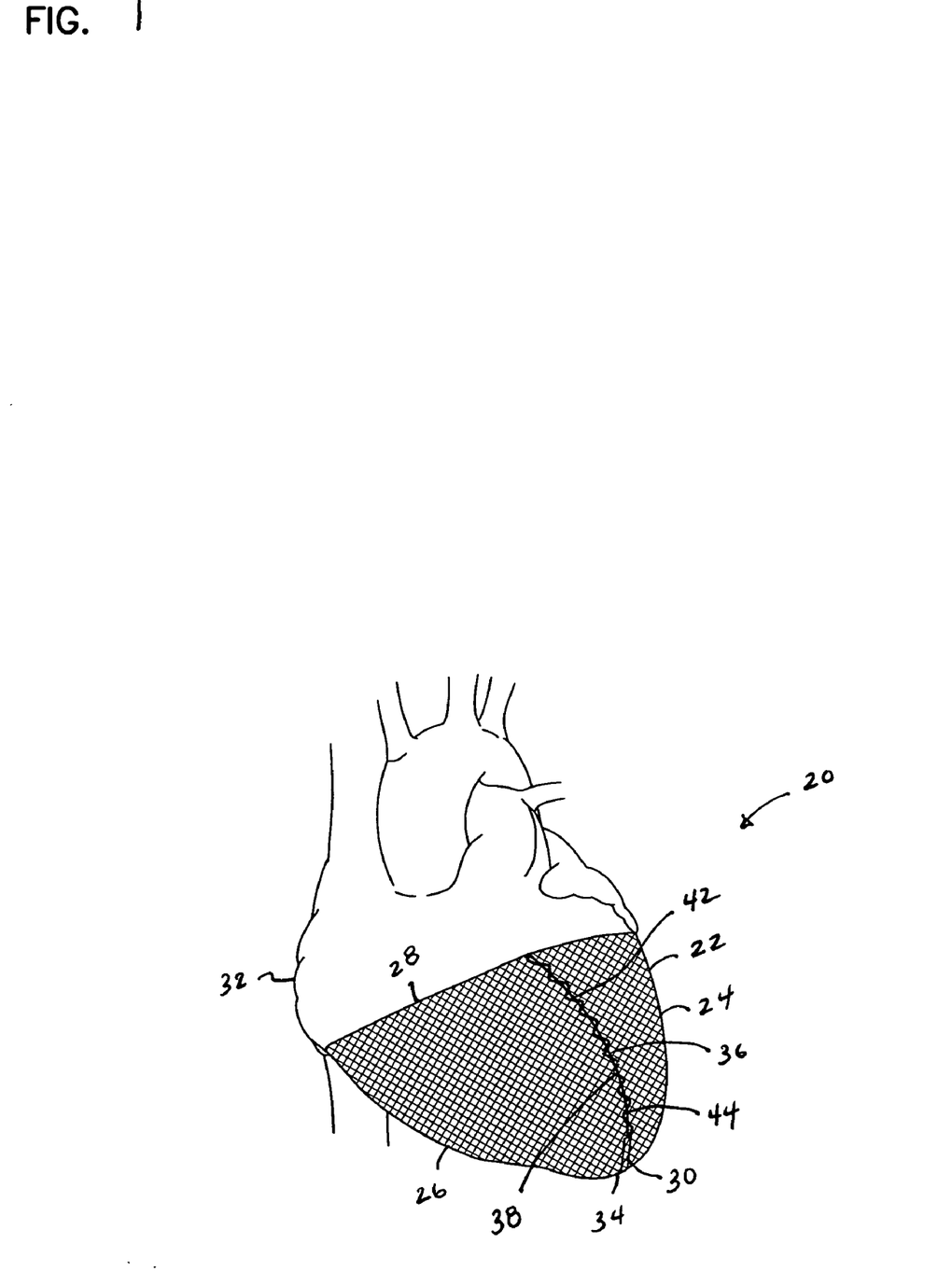
FIG. 1 is a schematic, perspective view of a heart with a cardiac support device secured thereto.
Figure 2:
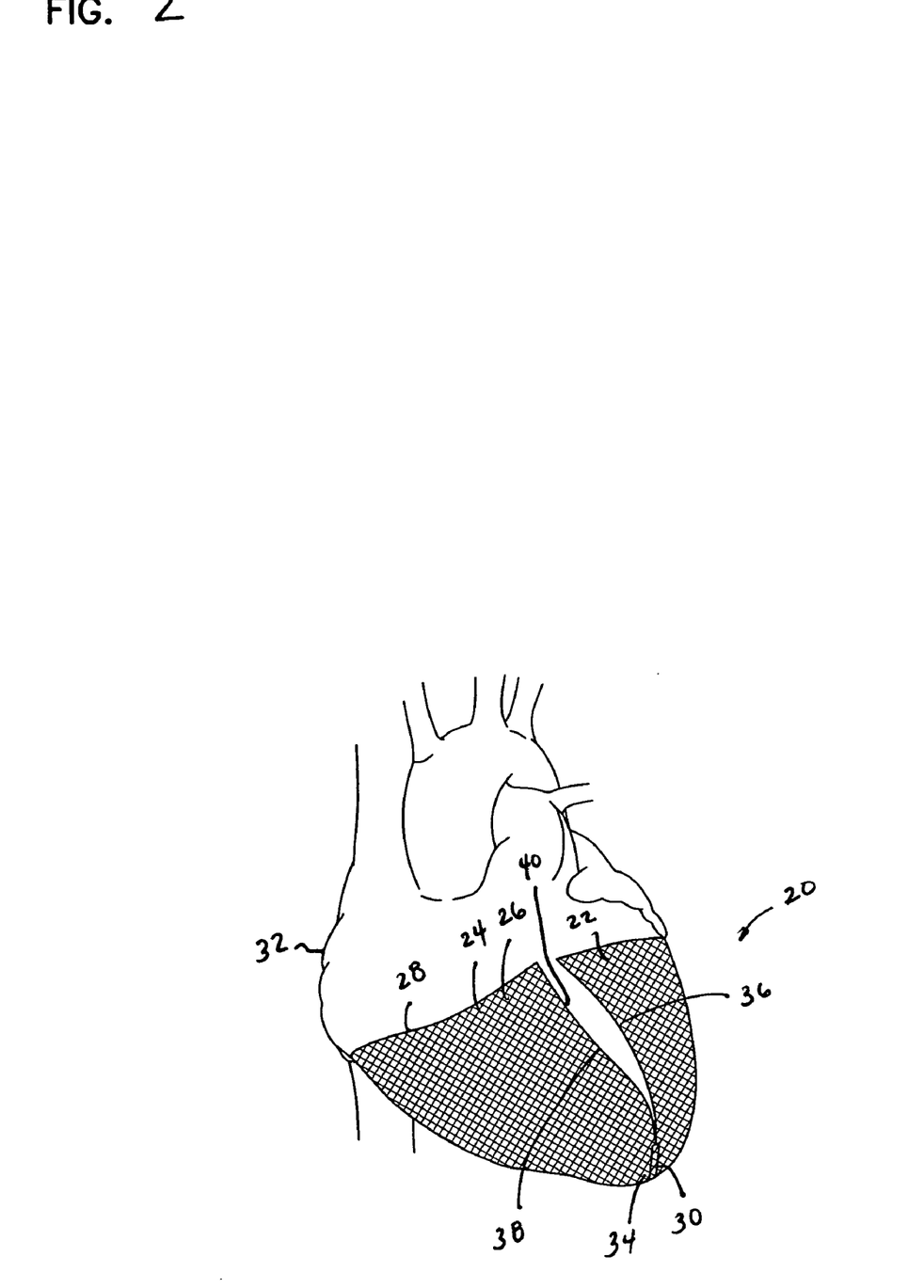
FIG. 2 is a schematic, perspective view of the heart and cardiac support device of FIG. 1, but showing the cardiac support device before being secured onto the heart.

For purposes of the method of this disclosure and the apparatus or device used for the method, many types of cardiac support devices 20 are useable. The particular cardiac support device 20 depicted in FIG. 1 is a jacket 22. Preferred jackets 22 will be constructed of a biologically compatible material. In preferred implementations, the jacket 22 is a knitted construction 24. In the specific example shown, the knitted construction 24 includes a continuous, flexible mesh net 26 having a base edge 28 and an opposite apex 30. It should be noted that the jacket 22 depicted in FIG. 1 is shown after placement onto a heart and secured thereto. FIG. 2 schematically shows the jacket 22 as it would appear loosely positioned around a heart 32 before being operably secured thereto (for example, with a seam in place and with excess material gathered). The base edge 28 can be seen forming a peripheral edge opposite from the apex 30, which is located in snugging engagement with the heart apex 34.

Still in reference to FIG. 1, the particular jacket 22 depicted in the drawings also includes a first lateral edge 36 and a second lateral edge 38 extending from the base edge 28. When wrapped around the heart 32, the jacket 22 is shaped such that the first lateral edge 36 and second lateral edge 38 are adjacent and opposing each other to define an open slot 40 (FIG. 2). In the cardiac support device 20 shown, the slot 40 generally extends from the base edge 28 and terminates at the apex 30. In other embodiments, jacket 22 is not slotted, but instead, forms a continuous surrounding enclosure for the heart 32. These other embodiments have the jacket 22 sized with excess material so that it can be loosely positioned over the heart 32.

In accordance with principles of this disclosure, a method is provided for operably securing the jacket 22 to the heart 32 after the cardiac support device 20 has been positioned around the heart 32. Various ways of positioning the cardiac support device 20 onto the heart 32 can be used. For example, the cardiac support device 20 can be placed around the heart 32 by the methods described in U.S. Pat. No. 6,293,906, incorporated herein by reference. In addition, methods can be used in accordance with the co-pending and commonly assigned U.S. patent application Ser. No. 10/663,623 filed Sep. 16, 2003, entitled "APPARATUS AND METHOD FOR APPLYING CARDIAC SUPPORT DEVICE", incorporated herein by reference.

Once the cardiac support device 20 is positioned around the heart 32, methods and apparatus in accordance with principles of this disclosure can be utilized to secure the cardiac support device 20 to the heart 32. In general, excess material in the jacket 22 is gathered and secured to other portions of the jacket 22 to prevent the jacket 22 from working loose from the heart 32. In one example, and in reference now to FIG. 2, once the cardiac support device 20 has been positioned over the heart 32, it will be resting on the heart 32 such that the slot 40 is open and, in the arrangement depicted, is on an anterior portion of the heart 32. To secure the jacket 22 shown in FIG. 2 to the heart 32, the slot 40 is closed. In one implementation, the slot 40 is closed by placing a closure 42 (FIG. 1) in the jacket 22 between the first lateral edge 36 and second lateral edge 38 to close the jacket 22 as shown in FIG. 1. In FIG. 1, closure 42 is depicted securing together the first lateral edge 36 and second lateral edge 38. In the particular arrangement shown in FIG. 1, the closure 42 is a seam 44.

Figure 4:
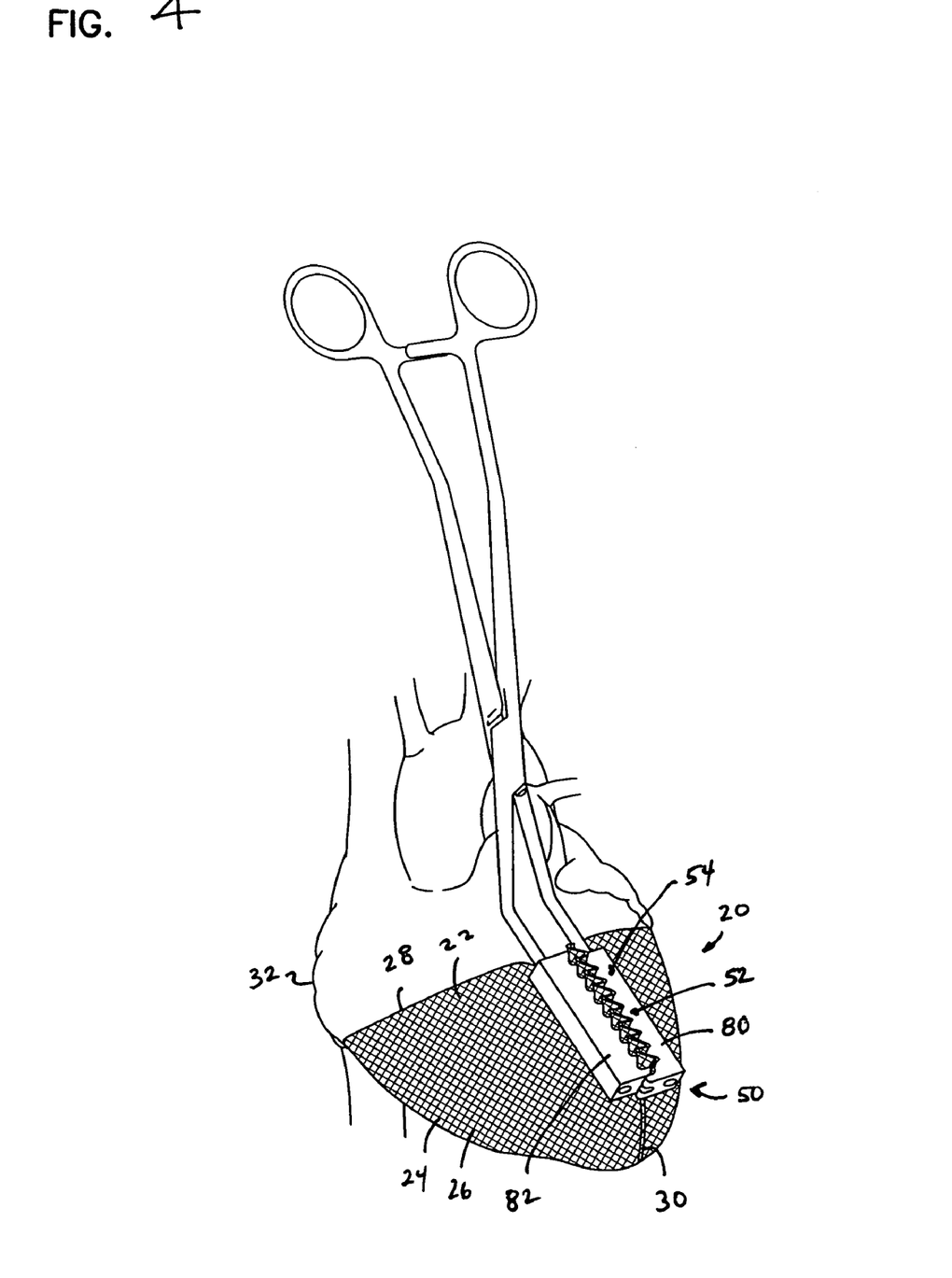
FIG. 4 is a schematic, perspective view of the heart and cardiac support device of FIG. 2 and showing another step of securing the cardiac support device to the heart.

In general, for the slotted cardiac support device 20 shown in FIG. 2, preferred methods include aligning at least a portion of the first lateral edge 36 and the second lateral edge 38 to form an aligned region 52 (FIG. 4). At this aligned region 52, a plurality of offsets 54 is simultaneously formed so that a fastener can be inserted through the offsets 54 to secure the first lateral edge 36 to the second lateral edge 38.

Figure 3:
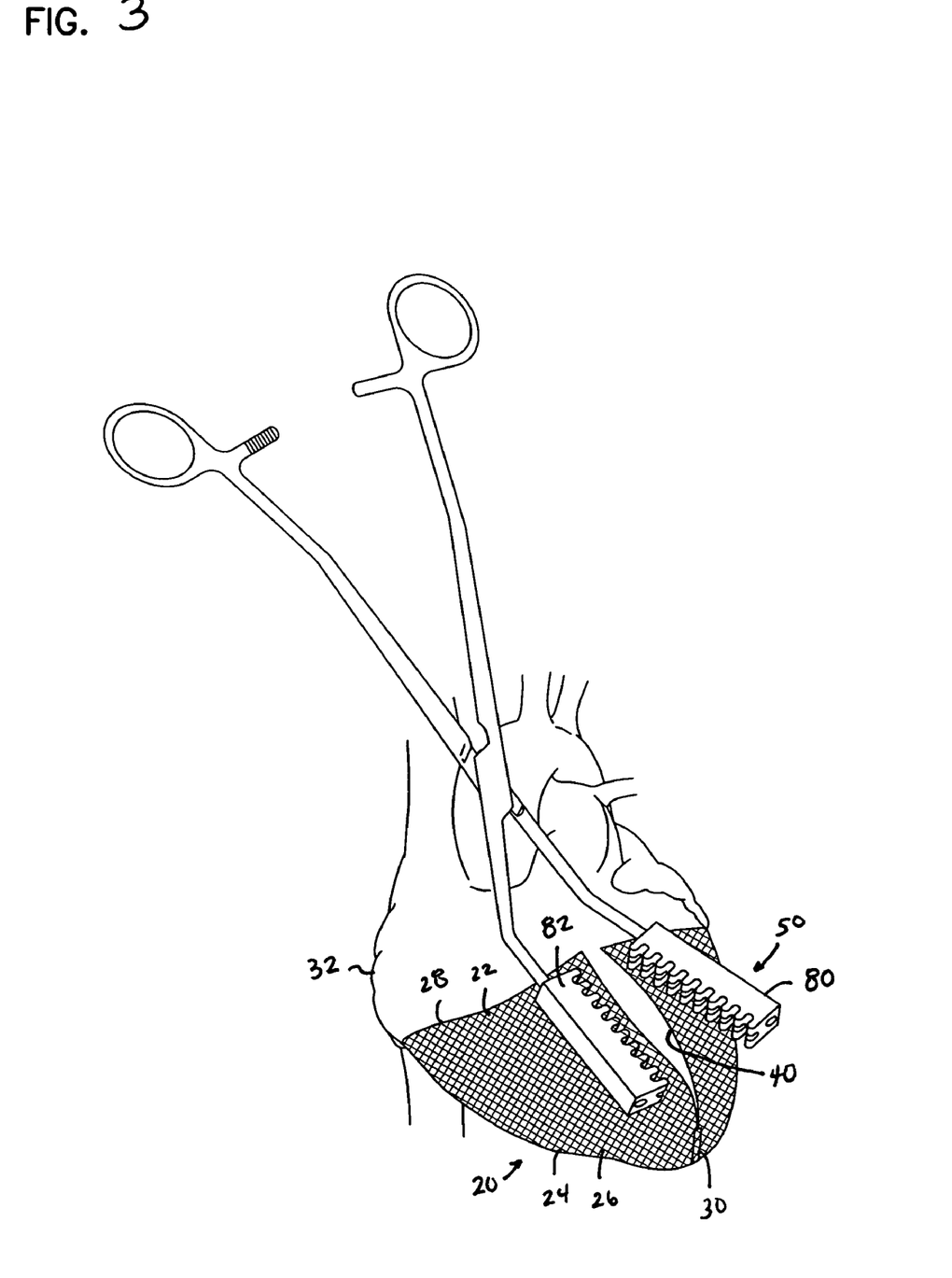
FIG. 3 is a schematic, perspective view of the heart and cardiac support device of FIG. 2 and depicting one step of securing the cardiac support device onto the heart.
Figure 5:
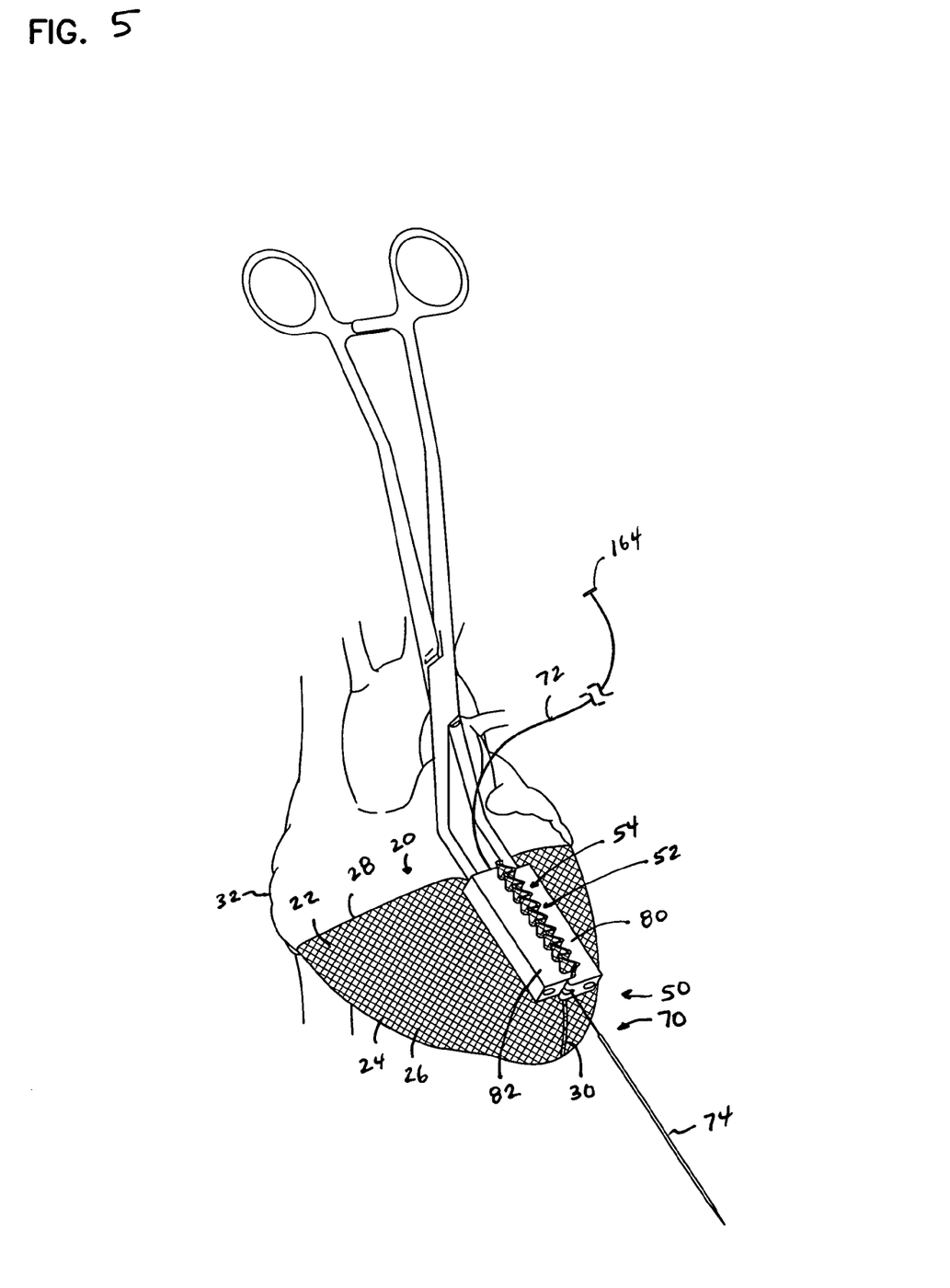
FIG. 5 is a schematic, perspective view of the heart and cardiac support device of FIG. 2 and showing another step of securing the cardiac support device to the heart.

Attention is directed to FIGS. 3-5, which show example steps for carrying out methods in accordance with the disclosure. In FIG. 3, the jacket 22 is shown with the slot 40 exposed. A device 50 is depicted approaching the jacket 22 in order to carry out subsequent steps to the method.

FIG. 4 depicts a step of aligning at least a portion of the first lateral edge 36 with a portion of the second lateral edge 38 to form aligned region 52. By "aligned region", it is meant a region of overlap of the jacket 22, and in the example shown, the overlap is between the first lateral edge 36 and the second lateral edge 38. FIG. 4 also depicts the steps of simultaneously forming pleats or a plurality of offsets 54 in the aligned region 52. By "offsets", it is meant portions of the jacket 22 along the aligned region that do not form a straight line. If the jacket 22 is a non-slotted version, the pleats or offsets are formed by gathering excess material (slack) in the jacket 22 along an aligned region (an overlapped region of material).

In one example method, the step of simultaneously forming a plurality of offsets 54 includes forming a plurality of undulations 56 in the aligned region 52. See FIG. 9. By "undulations", it is meant a wavy appearance, such that the aligned region 52 resembles a wave pattern 58. The particular wave pattern 58 depicted includes regular, continuous folds 60 in the aligned region 52. By "regular, continuous folds", it is meant that the wave pattern 58 includes alternating ridges 62 and troughs 64 repeating, without substantial modification in size and shape.

FIG. 5 shows another step to the method. In FIG. 5, a fastener 70 is inserted through the offsets 54 to secure the excess material to a remaining portion of the jacket 22. In the FIG. 5 embodiment, it secures the first lateral edge 36 to the second lateral edge 38. In the particular example depicted in FIG. 5, the fastener 70 includes a thread or suture 72. In the example shown in FIG. 5, the suture 72 is lead through the offsets 54 by a needle 74.

In general, the step of inserting the fastener 70 through the offsets 54 completes the closure 42, leaving seam 44 in place. The suture 72 can be knotted, tied, or secured in some fashion to the jacket 22.

As will be appreciated in connection with the example device 50 described below, in preferred methods, the step of forming an aligned region 52 and the step of simultaneously forming a plurality of offsets 54 are conducted concurrently (that is, at the same time, or simultaneously).

Figure 6:
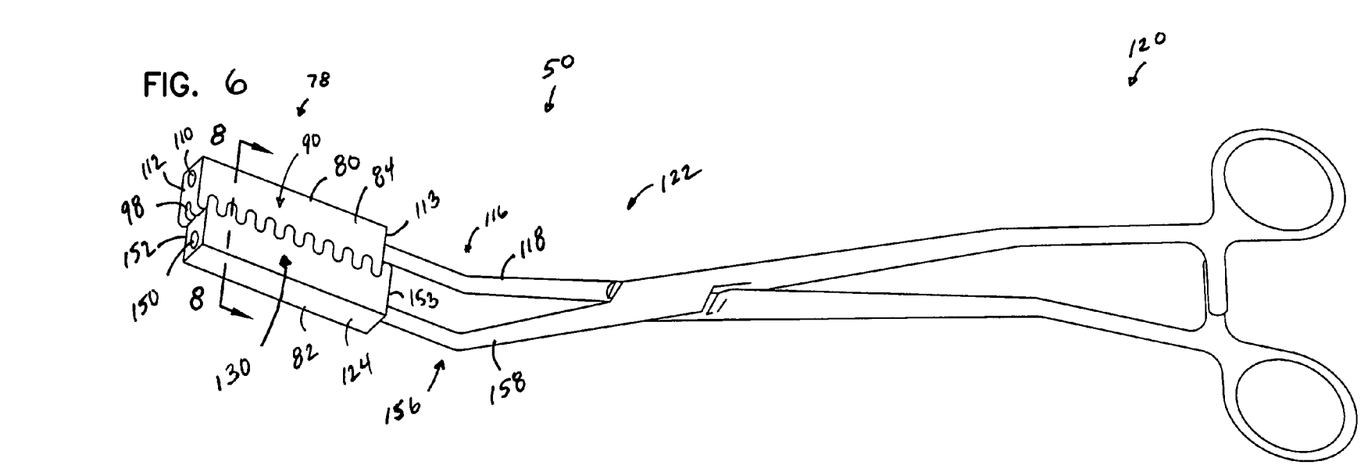
FIG. 6 is a perspective view of one embodiment of an apparatus useable to secure the cardiac support device to the heart, as depicted in FIGS. 1-5.
Figure 7:
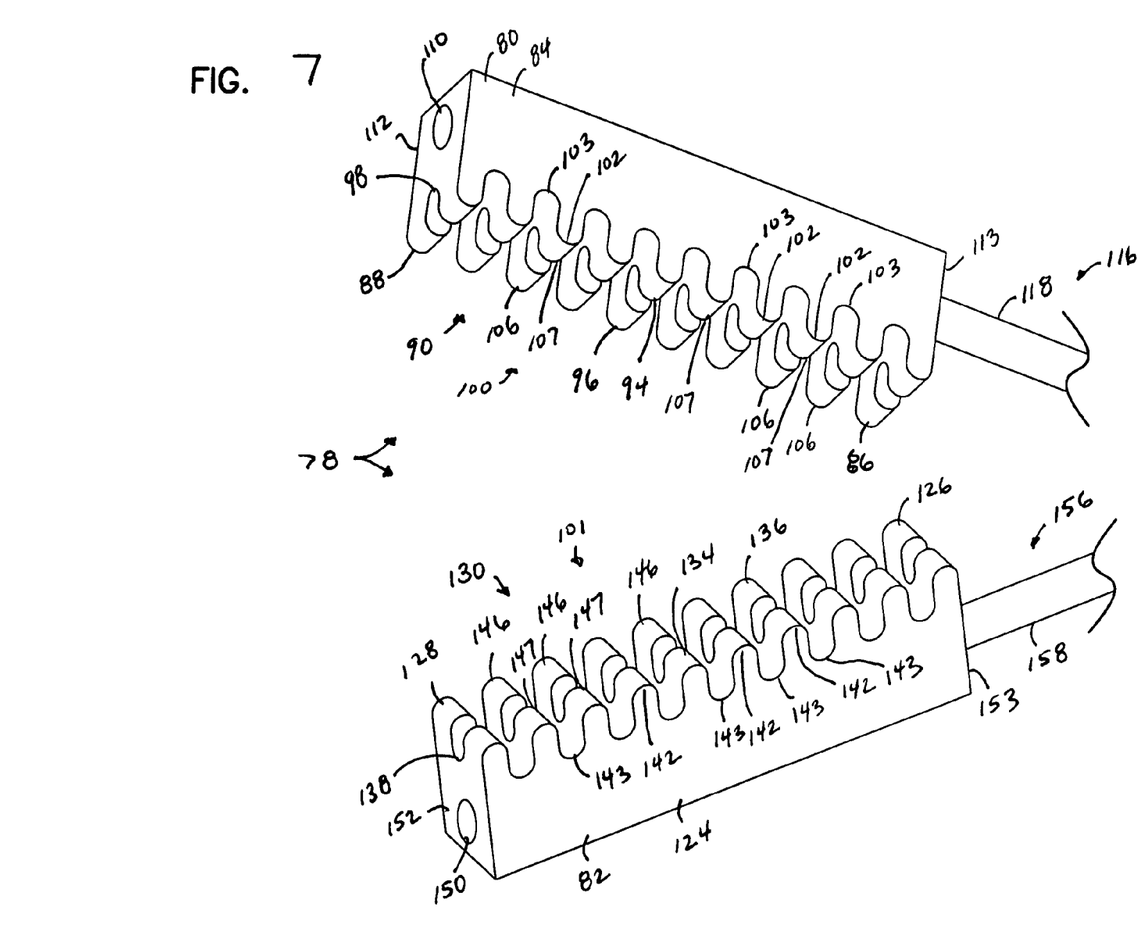
FIG. 7 is a perspective view of a portion of the apparatus depicted in FIG. 6.

In reference now to FIGS. 6-9, one embodiment of the device 50 that can be used in implementing the example methods described herein is depicted. The example device 50 illustrated includes a jaw arrangement 78 having a first clamp member 80 and a second clamp member 82. The first clamp member 80 and the second clamp member 82 are constructed and arranged to be moveable into and out of mateable engagement. FIGS. 4-6 and 9 illustrate the first clamp 80 and the second clamp member 82 in mateable engagement. FIGS. 3 and 7 show the first clamp 80 and second clamp member 82 out of mateable engagement.

Figure 10:
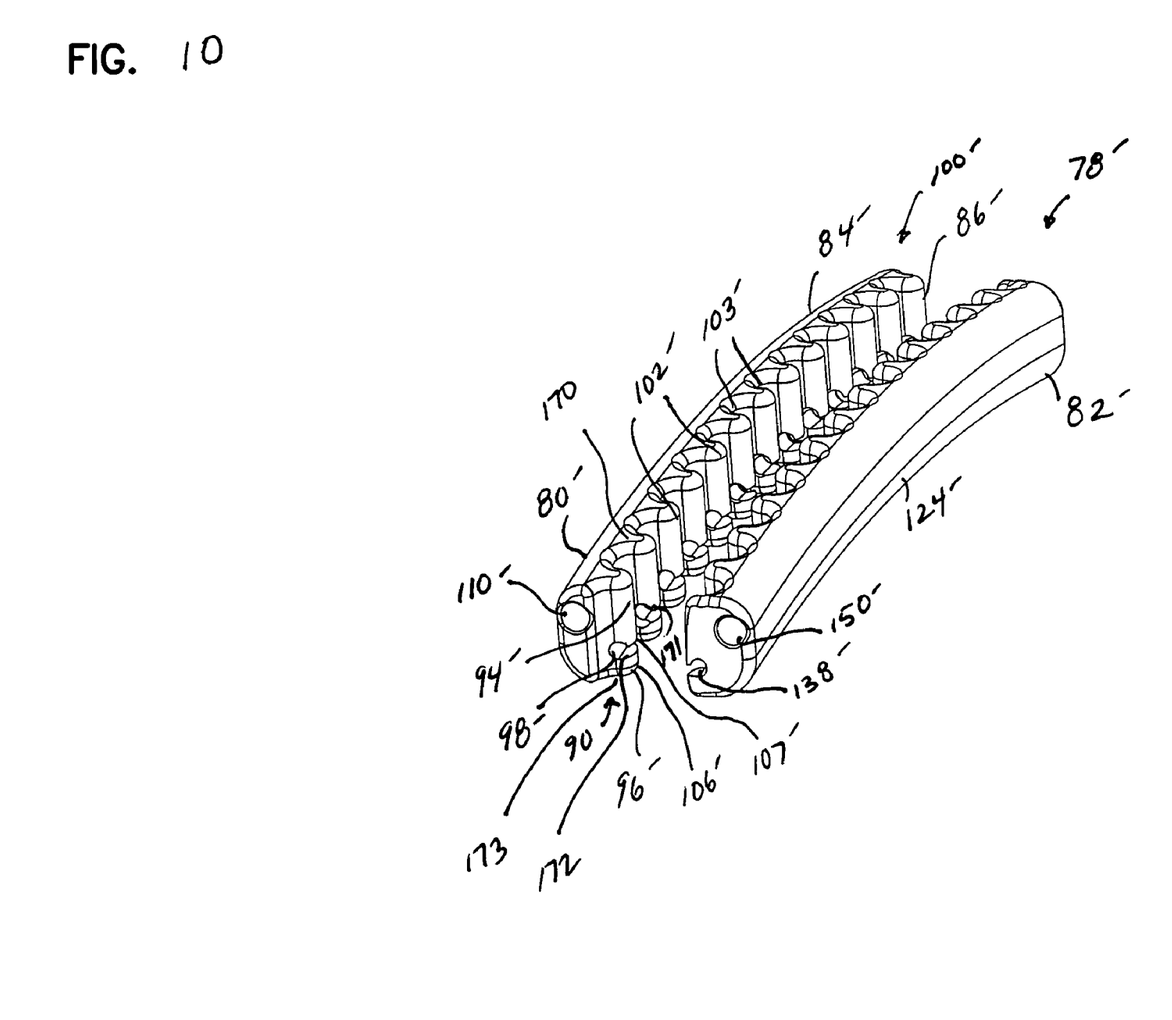
FIG. 10 is a perspective view of a portion of a second embodiment of an apparatus useable to secure the cardiac support device to the heart.

In reference now to FIG. 7, the first clamp member 80 is shown in perspective view. The first clamp member 80 depicted is generally a block 84 having a first engagement surface 86. The first engagement surface 86 is the surface that interacts with the second clamp member 82 when the clamp members 80, 82 are in mateable engagement. The block 84 depicted is a straight block, in that the points of the engagement surface 86 are co-planar. In other embodiments, the block 84 is curved, to match the outer contour of the heart 32. An example of a curved embodiment is illustrated in FIG. 10, described below.

The first engagement surface 86 includes at least two, spaced rows 88 of offset-forming structure 90. In the particular example, there is a first row 94 and laterally spaced from it, a second row 96. Each of the first row 94 and the second row 96 includes the offset-forming structure 90. The space between the first row 94 and second row 96 defines a first clamp member groove 98. The purpose of the clamp member groove 98 will become apparent below.

In the particular embodiment illustrated, the offset-forming structure 90 in the first row 94 includes pleat-forming members 100. The pleat forming members 100 have a height sufficient to gather excess material of the jacket 22. In the illustrated embodiment, the pleat forming members 100 are embodied as a row of alternating peaks 102 and valleys 103. Similarly, the offset-forming structure 90 in the second row 96 includes alternating peaks 106 and valleys 107. In the illustrated embodiment, the peaks 102 in the first row 94 are identical to and spaced directly across from the peaks 106 in the second row 96. Similarly, in the specific embodiment illustrated, the valleys 103 in the first row 94 are sized equally to and spaced directly across from the valleys 107 in the second row 96. As can also be seen in FIG. 7, in the example first clamp member 80 shown, the block 84 defines a first aperture 110 extending lengthwise through the block 84 between opposite ends 112, 113. In the embodiment shown, the aperture 110 runs generally parallel to the engagement surface 86. The aperture 110 can be used to accommodate holding structure 116. For example, in the embodiment shown, a rod or extension 118 of a medical tool 120 such as a clamp or tongs 122 is secured within the aperture 110.

FIG. 7 illustrates a perspective view of an example embodiment of the second clamp member 82. In general, in the particular embodiment illustrated, the first clamp member 80 and the second clamp member 82 are identical structures, and if made by molding, are made from the same mold. As such, the second clamp member 82 includes a block 124 having a second engagement surface 126. Again, although illustrated as straight in FIG. 7, in other embodiments, the clamp member 82 can be curved (see, e.g., FIG. 10, described below). The second engagement surface 126 includes at least two rows 128 of offset-forming structure 130. The row 128 includes third row 134 and fourth row 136. A second clamp member groove 138 is defined by the space between the third row 134 and fourth row 136. The third row 134 includes pleat forming members 100 embodied as alternating peaks 142 and valleys 143. The fourth row 136 includes alternating peaks 146 and valleys 147. There is also shown an aperture 150 extending between ends 152, 153 that can be used to accommodate holding structure 156 such as an extension 158 of the tool 120.

Figure 8:
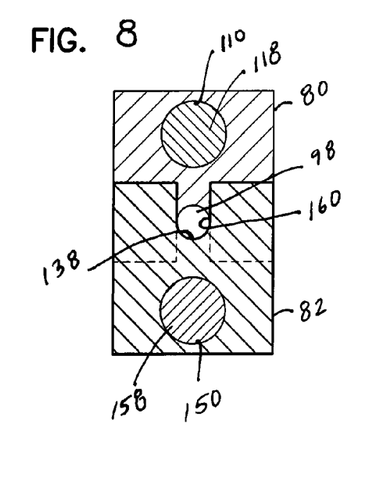
FIG. 8 is a cross-sectional view of the apparatus depicted in FIG. 6, the cross-section being taken along the line 8-8 of FIG. 6.
Figure 9:
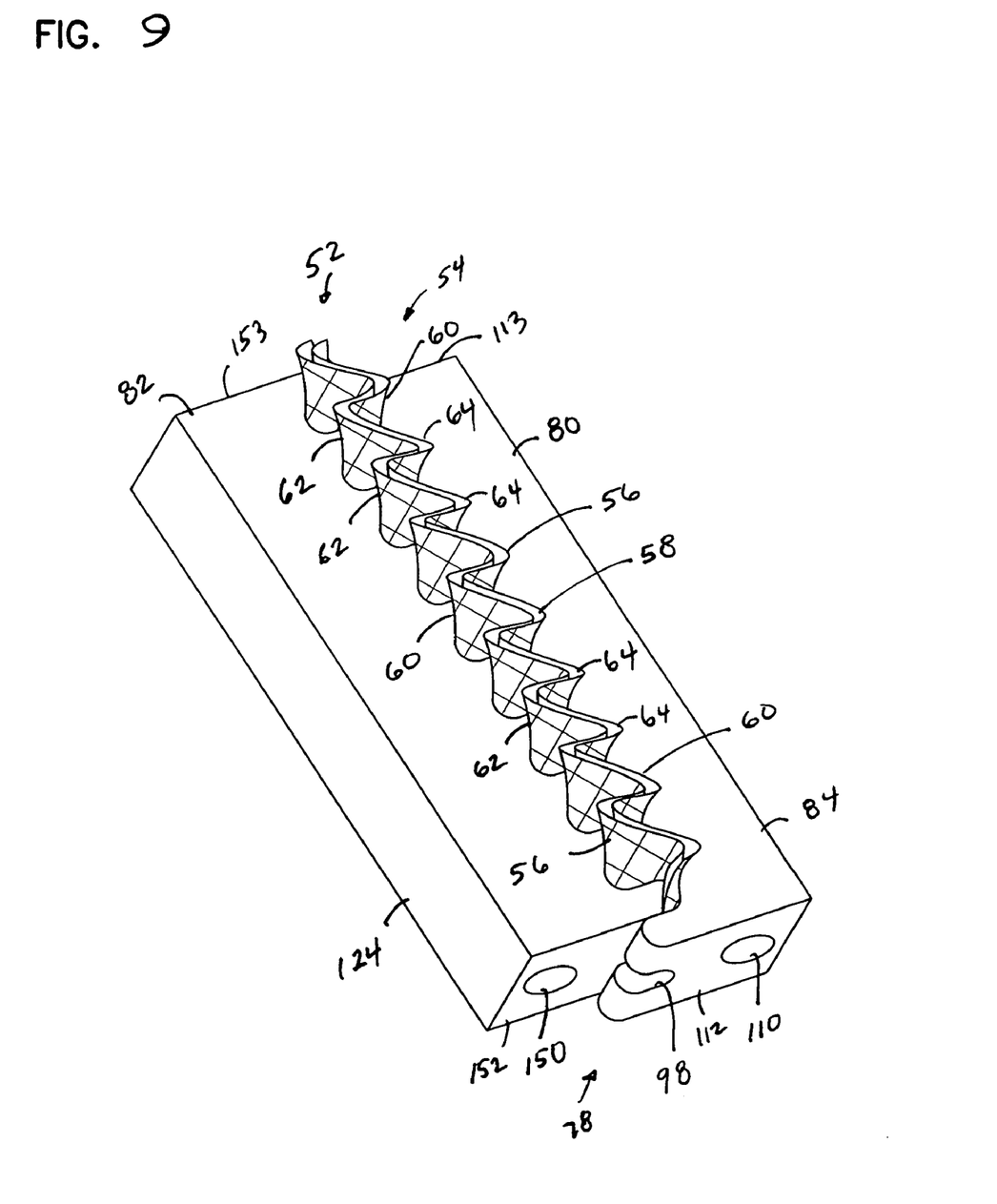
FIG. 9 is an enlarged, perspective view of a portion of FIG. 4.

FIGS. 6, 8, and 9 show the first clamp member 80 and second clamp member 82 in mateable engagement. The pleat forming members 100 cooperate with the pleat forming members 101 to form pleats with the excess material. In the example shown, mateable engagement includes the first row of peaks 102 projecting into the third row of valleys 143. The third row of peaks 142 is projecting into the first row of valleys 103. Similarly, the second row of peaks 106 is projecting into the fourth row of valleys 147, and the fourth row of peaks 146 is projecting into the second row of valleys 107. FIG. 9 shows how the aligned region 52 of the jacket 22 is squeezed or compressed between the first clamp member 80 and the second clamp member 82 to form the offsets 54. In particular, the offset-forming structure 90, 130 is shaped to result in the particular resulting offsets 54. Each of the peaks 102, 106, 142, 146 results in a corresponding trough 64 in the aligned region 52. Analogously, each of the valleys 103, 107, 143, 147 results in one of the ridges 62 in the aligned region 52.

Also, when the first clamp member 80 and the second clamp member 82 are in mateable engagement, the first clamp member groove 98 and the second clamp member groove 138 together form an open channel 160 (FIG. 8). By the term "open", it is meant that there is no portion of the first clamp member 80 and second clamp member 82 interfering or blocking the passage. However, in the preferred embodiment, the aligned region 52 extends through the open channel 160.

In the example shown, the needle 74 is passed through the open channel 160 with the attached suture 72. Because the aligned region 52 extends through the open channel 160, the suture 72 will be pulled through the offsets 84 in the aligned region 52. This results in seam 44. In other words, in the embodiment of FIG. 2 (the slotted jacket 22), the suture 72 passes through the jacket 22 along the first lateral edge 36 and then through the second lateral edge 38, then through the first lateral edge 36, then through the second lateral edge 38, etc.

In the embodiment shown in FIG. 6, the clamp or tongs 122 can be manipulated (open and closed) in order to move the first clamp member 80 and second clamp member 82 toward each other into mateable engagement and way from each other out of mateable engagement. Of course, in other embodiments, the first and second clamp members 80, 82 can be secured to other mechanisms or merely operated by hand.

While only two rows 88, 128 are shown in each of the clamp members 80, 82, if more than one seam 44 is desired, additional spaced rows can be added to the clamp members 80, 82. For example, if another row were added to each of the clamp members 80, 82, there would be an additional channel formed to accommodate another suture.

FIG. 10 illustrates a second embodiment of a jaw arrangement 78' having a first clamp member 80' and a second clamp member 82'. The first clamp member 80' and the second clamp member 82' are constructed analogously to the first clamp member 80 and second clamp member 82 described in FIGS. 6-9 above. The main difference between the embodiment of FIG. 10 and the embodiment of FIGS. 6-9 is that the first clamp member 80' and second clamp member 82' are curved to match the outer contour of the heart 32.

The first clamp member 80' depicted is generally a block 84' having a first engagement surface 86'. The first engagement surface 86' is the surface that interacts with the second clamp member 82' when the clamp members 80', 82' are in mateable engagement. The block 84' depicted is curved, in that the points of the engagement surface 86' are not contained in a single plane, but instead, follow a smooth curve. Preferably, the curve will follow the contour of the heart 32. In general, this curve will define a radius of at least 4 in., typically 6 in.-8 in., and generally not greater than 12 in.

The first engagement surface 86' includes at least two spaced rows of offset-forming structure 90. Illustrated in FIG. 10 is a first row 94' and a second row 96' laterally spaced from it. The space between the first row 94' and second row 96' defines a first clamp member groove 98'.

As with the embodiment of FIGS. 6-9, the offset-forming structure 90 in the first row 94' includes pleat forming members 100' embodied as a row of alternating peaks 102' and valleys 103'. Similarly, the offset-forming structure 90 in the second row 96' includes alternating peaks 106' and valleys 107'. The peaks 102' are identical to and spaced directly across from the peaks 106', with respect to the wave properties. However, the overall length of the peak 102' defined as between end 170 and end 171 is greater than the length of the peak 106' between end 172 and end 173. End 171 is the portion of the peak 102' that faces the groove 98'. End 172 is the portion of the peak 106' that faces the groove 98'. End 170 is depicted as an outer edge of the block 84', while end 173 forms the opposite edge of the block 84'.

Similarly, in the embodiment illustrated, the valleys 103' are sized equally and spaced directly across from the valleys 107' in the second row 96'. The length of the valleys 103' is greater than the length of the valleys 107'. The respective lengths are defined as between end 170 and end 171 for the valleys 103', and end 172 and end 173 for the valleys 107'.

As can also be seen in FIG. 10, the block 84' defines an aperture 110'. The aperture 110' has a curved contour. The aperture 110' can be used to accommodate holding structure, such as the holding structure 116, including rod 118 of medical tool 120, described above with respect to FIGS. 6-9.

The second clamp member 82' is also illustrated in FIG. 10. The second clamp member 82', in the embodiment shown, is identical to the first clamp member 80'. The embodiment of FIG. 10 shows the second clamp member 82' shows it made from a block 124' that has an outer, curved contour. As can be seen in FIG. 10, the second clamp member 82' defines a groove 138' and an aperture 150'. The second clamp member 82' includes two rows of offset-forming structure, identical to the structure described with respect to first clamp member 80'.

With respect to mateable engagement, forming offsets 54, accommodation of needle 74, manipulation of the clamp 80' and clamp 82', the FIG. 10 embodiment is the same as described with respect to FIGS. 6-9.

In reference again now to FIGS. 3-5, the example methods described above are shown implemented with the example device 50 of FIGS. 6-9. The methods described are also applicable to the embodiment of the clamp members 80', 82' of FIG. 10. In FIG. 4, the step of simultaneously forming a plurality of offsets 54 is illustrated as clamping excess material. In FIG. 4, this includes clamping the first lateral edge 36 and the second lateral edge 38. In particular, the step of clamping includes squeezing the excess material, for example the first lateral edge 36 and the second lateral edge 38, between opposing clamp members 80, 82. In the specific method illustrated, the step of squeezing includes squeezing the first lateral edge 36 and the second lateral edge 38 between opposing clamp members, each clamp member having a plurality of peaks and valleys.

FIG. 5 illustrates the step of inserting the needle 4 having suture 72 attached thereto through a passage or open channel 160 defined by the first clamp member 80 and the second clamp member 82.

In one example method, the step of inserting the needle 74 having the suture 72 attached thereto includes pulling the suture 72 through the offsets 54 until a T-bar 164 secured to the suture 72 engages or abuts one of the first clamp member 80 and the second clamp member 82. The first and second clamp members 80, 82 would then be released and moved out of mateable engagement. The end with the T-bar 164 would not need further attachment or securing to the jacket 22. The opposite end of the seam 44 could be further secured to the jacket by knotting, tying, or other methods. As can be seen in FIG. 1, the resulting seam 44, in the particular example shown, includes securing an entire length of the excess material to other portions of the jacket 22. For the FIG. 2 embodiment of the jacket 22, this includes securing the first lateral edge 36 to the second lateral edge 38 from the apex 30 to the base edge 28.

Many embodiments can be made in accordance with the principles of this disclosure.

We claim:

1. A method for operably securing a cardiac support device around a mammalian heart; the cardiac support device being loosely positioned over the heart; the cardiac support device including a jacket constructed of a flexible material; the method comprising:
    (a) simultaneously forming a plurality of offsets in the jacket material; and
    (b) inserting a fastener through the offsets.

2. A method according to claim 1 wherein:
    (a) said step of inserting a fastener includes inserting a suture through the offsets.

3. A method according to claim 1 wherein:
    (a) said step of inserting a fastener includes inserting a needle with a suture attached thereto through the offsets.

4. A method according to claim 1 wherein:
    (a) said step of simultaneously forming a plurality of offsets includes forming a plurality of undulations.

5. A method according to claim 4 wherein:
    (a) said step of simultaneously forming a plurality of undulations includes forming a plurality of regular, continuous folds in the jacket material.

6. A method according to claim 5 wherein:
    (a) said step of simultaneously forming a plurality of offsets includes clamping together jacket material.

7. A method according to claim 6 wherein:
    (a) said step of clamping includes squeezing the jacket material between opposing clamp members.

8. A method according to claim 7 wherein:
    (a) said step of squeezing includes squeezing the jacket material between first and second opposing clamp members;
        (i) the first clamp member having a first plurality of peaks and valleys;
        (ii) the second clamp member having a second plurality of peaks and valleys;
            (A) the second plurality of peaks sized and arranged to mateably engage the first plurality of valleys; and
            (B) the second plurality of valleys sized and arranged to mateably engage the first plurality of peaks.

9. A method according to claim 8 wherein:
    (a) said step of inserting a fastener through the offsets includes inserting a needle having a suture attached thereto through a passage defined by the first clamp member and the second clamp member.

10. A method according to claim 9 further including:
    (a) after said step of inserting a fastener, releasing the first clamp member and the second clamp member from the cardiac support device.

11. A method according to claim 9 wherein:
    (a) said step of inserting a needle having a suture attached thereto includes pulling the suture through the offsets until a T-bar secured to the suture abuts one of the first clamp member and second clamp member.

12. A method according to claim 1 wherein:
    (a) the jacket includes material having first and second lateral edges defining a slot therebetween; and
    the method further comprises:
    (b) aligning at least a portion of the first lateral edge with at least a portion of the second lateral edge to form an aligned region.

13. A method according to claim 12 wherein:
    (a) said step of aligning is conducted concurrently with said step of simultaneously forming a plurality of offsets.

14. A method according to claim 12 wherein:
    (a) said step of simultaneously forming a plurality of offsets includes clamping the first lateral edge and the second lateral edge together.

15. A method according to claim 12 wherein:
    (a) said step of inserting a fastener through the offsets includes inserting a suture through the offsets to secure the first lateral edge to the second lateral edge.

16. A method according to claim 15 wherein:
    (a) the cardiac support device includes a jacket comprising a continuous flexible mesh net with a base edge, an opposite apex, the first and second lateral edges extending from the base edge, and the open slot extending between the first and second lateral edges from the base edge and terminating at the apex; and
    (b) said step of inserting a fastener through the offsets to secure the first lateral edge to the second lateral edge includes securing an entire length of the first lateral edge to the second lateral edge from the apex to the base edge.

* * * * *